US008507225B2

(12) United States Patent
Yasuno et al.

(10) Patent No.: US 8,507,225 B2
(45) Date of Patent: Aug. 13, 2013

(54) OLIGONUCLEOTIDES FOR GENOTYPING THYMIDYLATE SYNTHASE GENE

(75) Inventors: Hideyuki Yasuno, Kanagawa (JP); Kazushige Mori, Kanagawa (JP)

(73) Assignee: F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 13/027,751

(22) Filed: Feb. 15, 2011

(65) Prior Publication Data

US 2011/0177507 A1 Jul. 21, 2011

Related U.S. Application Data

(62) Division of application No. 10/529,713, filed as application No. PCT/JP02/10167 on Sep. 30, 2002, now Pat. No. 7,919,235.

(51) Int. Cl.
*C12P 19/34* (2006.01)

(52) U.S. Cl.
USPC ........................................ 435/91.2; 435/6.12

(58) Field of Classification Search
None
See application file for complete search history.

(56) References Cited

U.S. PATENT DOCUMENTS

| 6,174,670 | B1 | 1/2001 | Wittwer et al. |
| 6,664,064 | B1 | 12/2003 | Dietmaier |
| 2004/0219557 | A1 | 11/2004 | Dobrowolski et al. |

FOREIGN PATENT DOCUMENTS

| EP | 1 207 210 | 5/2002 |
| EP | 1207210 A1 | 5/2002 |
| JP | 2002-191384 | 7/2002 |
| WO | WO 00/23112 | 4/2000 |
| WO | WO 00/23112 A1 | 4/2000 |
| WO | WO 01/36686 | 5/2001 |
| WO | WO 01/36686 A2 | 5/2001 |

OTHER PUBLICATIONS

Wittwer et al. (2001) Methods vol. 25, 430-442.*
Kawakami et al. Anticancer Research (1999) vol. 19:3249-3252.*
Marsh et al. (Nov. 2001) Clinical Colorectal Cancer vol. 1 No. 3: 175-178.*
Luo et al. (2002) Biochemical Genetics vol. 40 No. 1/2 pp. 41-51.*
Danenberg, "Thymidylate Synthetase—A Target in Cancer Chemotherapy" Biochimica et Biophysica Acta. vol. 473:73-92 (1977).
Etienne et al., "Prognostic Value of Tumoral Thymidylate Synthase and p53 in Metastatic Colorectal Cancer Patients Receiving Fluorouracil-Based Chemotherapy: Phenotypic and Genotypic Analyses" Journal of Clinical Onocology vol. 20:2832-2843 (2002).
GenBank Accession No. AF279906, "*Homo sapiens* thymidylate synthase (TSER) gene, TSER-3 allele, partial sequence." (2000).
Heidelberger, et al., "Fluorinated Pyrimidines, A New Class of Tumour-Inhibitory Compounds" Nature vol. 179:663-666 (1957).

(Continued)

*Primary Examiner* — Samuel Woolwine
*Assistant Examiner* — Suchira Pande
(74) *Attorney, Agent, or Firm* — Fish & Richardson P.C.

(57) ABSTRACT

Oligonucleotides for genotyping the thymidylate synthase gene are provided. The number of tandem repeats in the promoter region of the thymidylate synthase gene can be identified based on the hybridization of an oligonucleotide of the invention to the genomic DNA of a subject. Therefore, the genotype of the thymidylate synthase gene can be identified based on the number of tandem repeats. The genotype relates to the responsiveness of a subject towards an antitumor agent.

62 Claims, 1 Drawing Sheet

(56) References Cited

OTHER PUBLICATIONS

Horie et al., "Characterization of regulatory sequences and nuclear factors that function in cooperation with the promoter of the human thymidylate synthase gene" Biochimica et Biophysica Acta. vol. 1216:409-416 (1993).
Horie et al., "Functional analysis and DNA polymorphism of the tandemly repeated sequences in the 5'-terminal regulatory region of the human gene for thymidylate synthase." Cell Struct Funct. vol. 20:191-197 (1995).
Kawakami et al., "Different Lengths of a Polymorphic Repeat Sequence in the Thymidylate Synthase Gene Affect Thrnslational Efficiency but Not Its Gene Expression" Clinical Cancer Reasearch vol. 7:4096-4101 (2001).
Krajinovic et al., "Polymorphism of the thymidylate synthase gene and outcome of acute lymphoblastic leukaemia" The Lancet vol. 359:1033-1034 (2002).
Luo et al., "Length polymorphism of thymidylate synthase regulatory region in Chinese populations and evolution of the novel alleles." Biochemical Genetics vol. 40:41-51 (2002).
Luo et al., EMBL Accession No. AF279907 (2001).
Marsh et al., "Ethnic variation in the thymidylate synthase enhancer region polymorphism among Caucasian and Asian populations," *Genomics*, vol. 58(3) pp. 310-312, 1999.
Marsh et al., EMBL Accession No. AF127519 (1999).
Pals et al., "Detection of a single base substitution in a single cell using the LightCycler," *J. Biochem. Biophys. Methods*, 47: pp. 121-129, 2001.
Park et al., "Thymidylate synthase gene polymorphism predicts response to capecitabine in advanced colorectal cancer" Int J Colorectal Dis vol. 17:46-49 (2002).
Peters et al., "Induction of thymidylate synthase as a 5-fluorouracil resistance mechanism" Biochimica et Biophysica Acta vol. 1587:194-205 (2002).
Pullarkat et al., "Thymidylate synthase gene polymorphism determines response and toxicity of 5-FU chemotherapy" The Pharmacogenomics Journal vol. 1:65-70 (2001).
Stratagene catalog 1988.
Ulrich et al., "Thymidylate Synthase Promoter Polymorphism, Interaction with Folate Intake, and Risk of Colorectal Adenomas" Cancer Research vol. 62:3361-3664 (2002).
von Ahsen et al. "DNA Base Bulge vs. Unmatched End Formation in Probe-based Diagnostic Insertion/Deletion Genotyping: Genotyping the UGTIAI (TA)n Polymorphism by Real-Time Fluorescence PCR" Clinical Chemistry vol. 46:1939-1945 (2000).
USPTO Restriction Requirement in U.S. Appl. No. 10/529,713, mailed May 15, 2008, 6 pages.
Fish & Richardson P.C., Amendment and Response to Restriction Requirement dated May 15, 2008 in U.S. Appl. No. 10/529,713, filed Jul. 15, 2008, 12 pages.
USPTO Non Final Office Action in U.S. Appl. No. 10/529,713, mailed Oct. 29, 2008, 32 pages.
Fish & Richardson P.C., Amendment and Response to Office Action dated Oct. 29, 2008 in U.S. Appl. No. 10/529,713, filed Mar. 27, 2009, 13 pages.
USPTO Final Office Action in U.S. Appl. No. 10/529,713, mailed Jun. 25, 2009, 28 pages.
Fish & Richardson P.C., Request for Continued Examination; Amendment and Response to Office Action dated Jun. 25, 2009 in U.S. Appl. No. 10/529,713, filed Dec. 23, 2009, 24 pages.
Notice of Allowance in U.S. Appl. No. 10/529,713, mailed Nov. 15, 2010, 8 pages.
Fish & Richardson P.C., Response to Notice of Allowance dated Nov. 15, 2010 in U.S. Appl. No. 10/529,713, filed Feb. 14, 2011, 2 pages.
Buck et al., "Design Strategies and Performance of Custom DNA Sequencing Primers," BioTechniques, 27:528-536 (1999).
GenBank Accession No. AF127520 (Jul. 21, 1999).
Interview Summary of Nov. 2, 2009, in U.S. Appl. No. 10/529,713, issued on Nov. 5, 2009.
Interview Summary of Oct. 26, 2010, in U.S. Appl. No. 10/529,713, mailed Nov. 1, 2010.
Kawakami et al., "Different Lengths of a Polymorphic Repeat Sequence in the Thymidylate Synthase Gene Affect Translational Efficiency but Not Its Gene Expression" *Clinical Cancer Reasearch* vol. 7:4096-4101 (2001).
Kawakami et al., "Polymorphic tandem repeats in the thymidylate synthase gene is associated with its protein expression in human gastrointestinal cancers." *Anticancer Research* vol. 19:3249-52 (1999).
Marsh et al., "Ethnic variation in the thymidylate synthase enhancer region polymorphism among Caucasian and Asian populations." *Genomics* vol. 58:310-312 (1999).
Pals et al., J. Biochem, Biophys. Methods 47:121-129 (2001).
Stratagene Catalog (1998).
von Ahsen et al. "DNA Base Bulge vs. Unmatched End Formation in Probe-based Diagnostic Insertion/Deletion Genotyping: Genotyping the *UGTIAI* (TA)$_n$ Polymorphism by Real-Time Fluorescence PCR" *Clinical Chemistry* vol. 46:1939-1945 (2000).
Restriction Requirement issued on May 15, 2008 in U.S. Appl. No. 10/529,713.
Fish & Richardson P.C., Response to Restriction Required in U.S. Appl. No. 10/529,713, filed on Jul. 15, 2008.
Non-Final Office Action issued on Oct. 29, 2008 in U.S. Appl. No. 10/529,713.
Fish & Richardson P.C., Response to Non-Final Office Action issued in U.S. Appl. No. 10/529,713, filed on Mar. 27, 2009.
Final Office Action issued on Jun. 25, 2009 in U.S. Appl. No. 10/529,713.
Fish & Richardson P.C., Request for Continued Examination and Amendment for U.S. Appl. No. 10/529,713, filed on Dec. 23, 2009.
Notice of Allowance and Issue Fee Due in U.S. Appl. No. 10/529,713, mailed Nov. 15, 2010.
International Search Report and International Preliminary Examination Report; Application No. PCT/JP02/10167; mailing date Jun. 13, 2003; 6 pages.

\* cited by examiner

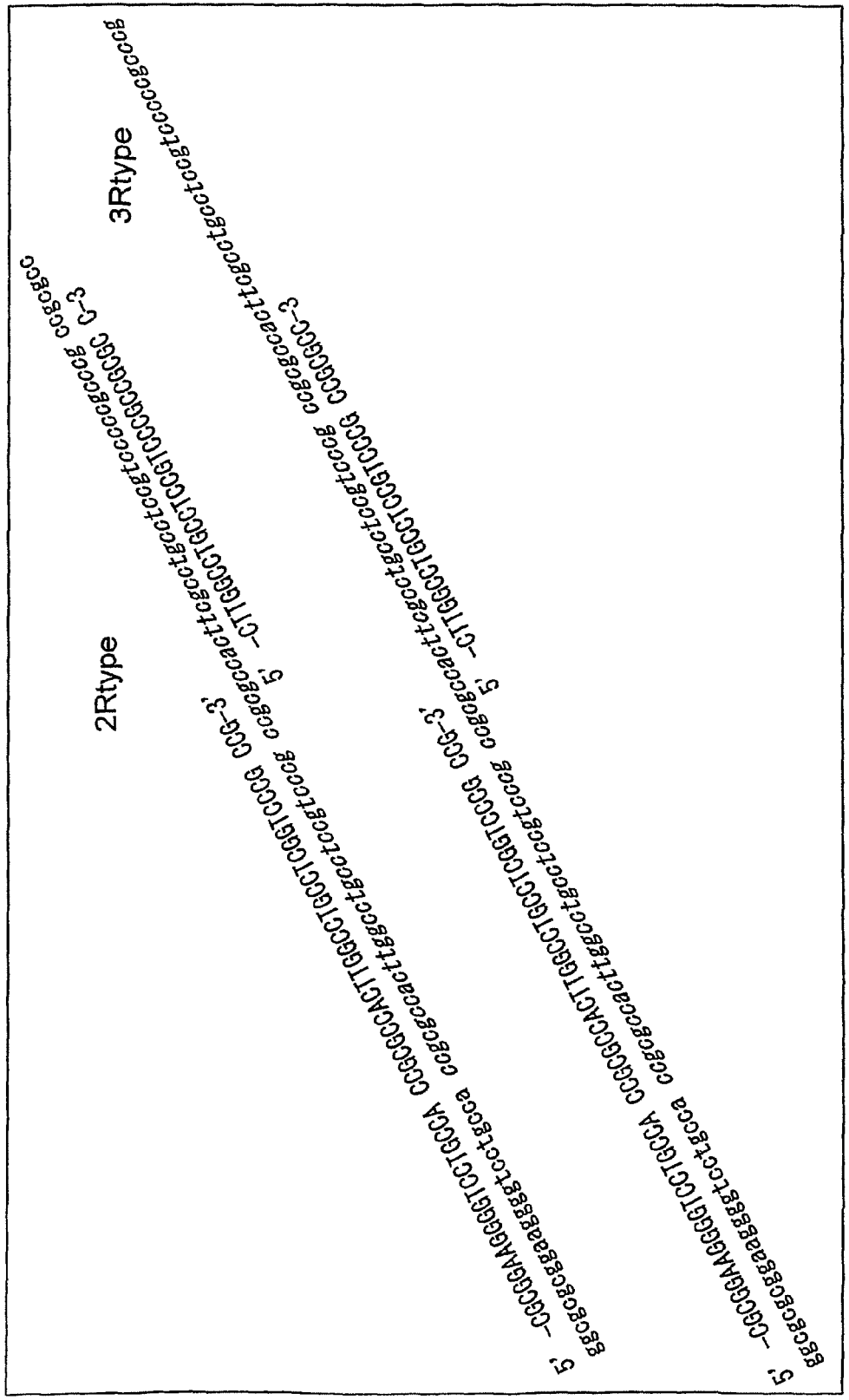

OLIGONUCLEOTIDES FOR GENOTYPING THYMIDYLATE SYNTHASE GENE

CROSS-REFERENCE TO RELATED APPLICATIONS

This application is a divisional of U.S. application Ser. No. 10/529,713, filed on Mar. 29, 2005, now U.S. Pat. No. 7,919,235, which is the National Stage of International Application No. PCT/JP2002/010167, filed Sep. 30, 2002. The contents of these applications are incorporated by reference herein in their entirety.

TECHNICAL FIELD

The present invention relates to the genotyping of the thymidylate synthase gene. The present invention also relates to the prediction of the responsiveness of a subject towards an antitumor agent based on the thymidylate synthase genotype.

BACKGROUND

5-Fluorouracil (5-FU) is a compound that has been utilized as an antitumor agent for a long time (Heidelberger C, Chaudhuri N K, Danenberg P V, Mooren D, et al. (1957) Fluorinated pyrimidines: a new class of tumor inhibitory compounds. Nature 179:663-666). The antitumor effects of 5-FU against various tumors have been reported.

The cytotoxic effect of 5-FU is based on the inhibition of DNA synthesis in cells. 5-FU inhibit even the DNA synthesis in non-tumor tissue not only that in tumor tissue. However, since usually a far more active DNA synthesis takes place in tumor tissues compared to non-tumor tissues, the manifested influence of the 5-FU-mediated inhibitory action is thought to be comparatively larger in tumor tissues. It is through this mechanism that 5-FU exerts an inhibitory action on tumor tissues.

On the other hand, the administration of 5-FU, which is a cytotoxic agent, often accompanies adverse effects that cannot be ignored. The cytotoxic effect of 5-FU disables not only tumor tissues, but also non-tumor tissues. 5-FU sensitivity in 5-FU administered patients is considered to be closely related to the magnitude of the adverse effects of the drug.

5-FU is a DNA synthesis inhibitor that targets thymidylate synthase. Thymidylate synthase catalyzes the intracellular conversion of deoxyuridylate to deoxythymidylate. Deoxythymidylate is the only de novo source of thymidylate, an essential precursor for DNA synthesis (Danenberg PV (1997) Thymidylate synthase. a target enzyme in cancer chemotherapy. Biochim Biophys Acta 473:73-92).

The promoter of thymidylate synthase gene has been demonstrated to be polymorphic (Nobuyuki H, Masahiko C, Ryushi N, Keiichi T (1993) Characterization of the regulatory sequences and nuclear factors that function in cooperation with the promoter of the human thymidylate synthase gene. Biochim Biophys Acta 1216:409-416). Furthermore, it has been shown that the polymorphism of the thymidylate synthase gene promoter is related to the response of a subject towards 5-FU. Human thymidylate synthase gene has a polymorphism comprising two or three tandem repeats of a 28-bp sequence in its regulatory region. The expression level of the thymidylate synthase gene which is homozygous for three tandem repeats, is 3.6 times that of the thymidylate synthase gene which is homozygous for two tandem repeats. As a result, subjects carrying the three tandem repeats have significantly fewer adverse effects (Pullarkat, S T, Stoehlmacher J, Ghaderi V, Xiong Y, et al. (2001) Thymidylate synthase gene polymorphism determines clinical outcome of patients with colorectal cancer treated with fluoropyrimidine chemotherapy. Pharmacogenomics J 1:65-70).

Thymidylate synthase is an important target of not only 5-FU, but also other antitumor agents. For example, capecitabine, which was developed as an oral prodrug of 5-FU, also targets thymidylate synthase. This suggested that the polymorphism in the regulatory region of the human thymidylate synthase gene is a useful marker for determining the responsiveness of a subject towards antitumor agents.

SUMMARY

An objective of the present invention is to provide a method for genotyping the thymidylate synthase gene. Especially, oligonucleotides suitable for genotyping the thymidylate synthase gene are provided. Another objective of the present invention is to provide a method for predicting the responsiveness of a subject towards an antitumor agent that targets thymidylate synthase based on the thymidylate synthase genotype.

It has been demonstrated that the polymorphism of tandem repeats in the promoter region of the thymidylate synthase gene is related to the responsiveness of a subject against antitumor agents that target thymidylate synthase. Therefore, the effectiveness or the degree of adverse effects of an antitumor agent can be predicted by analyzing this polymorphism. Polymorphism is generally determined by amplifying genomic DNA and analyzing amplicon size. The size of amplicons amplified by PCR is analyzed by gel electrophoresis. However, gel electrophoresis is a laborious and time-consuming analytical technique. Antitumor agents that target thymidylate synthase are important drugs in the chemotherapy of cancer. Therefore, a method that more conveniently yields information regarding the responsiveness of a subject against an antitumor agent that targets thymidylate synthase is desired.

Extensive research was carried out by the present inventors on a method for identifying the number of tandem repeats in the promoter region of the thymidylate synthase gene. As a result, they discovered that the number of tandem repeats in genomic DNA can be identified by using an oligonucleotide having a specific nucleotide sequence as a probe, and detecting mismatches therein. Furthermore, the present inventors confirmed that the genotype of the subject could be determined based on the number of tandem repeats elucidated as above. Furthermore, the present inventors discovered that it is possible to design a strategy for treating a cancer in a patient by relating thymidylate synthase genotype, which is determined by the present invention, with the responsiveness of the subject against antitumor agents targeting thymidylate synthase.

Namely, the present invention provides an isolated oligonucleotide that
  (a) comprises a nucleotide sequence that is complementary to a region consisting of:
    (i) the central repeat unit of three repeat units composing a tandem repeat in the promoter region of the thymidylate synthase gene, and
    (ii) the repeat unit located downstream of the central repeat unit, and
  (b) hybridizes to the region of (a) under highly stringent hybridization conditions.

As mentioned earlier, the tandem repeat in the promoter region of the thymidylate synthase gene is polymorphic. Namely, the presence of two kinds of tandem repeats, a tandem repeat consisting of two repeat units, and a tandem repeat consisting of three repeat units, has been elucidated. "Tandem repeat" as mentioned herein refers to a region in which two or more similar nucleotide sequences repeat successively. Similar repeating nucleotide sequences are called repeat units. Generally, the number of repeats is 2 or more. In the present invention, the number of repeats to be identified is 2 and 3. Hereinafter, a polymorphic form in which three repeat units compose a tandem repeat will be referred to as 3R. Furthermore, a polymorphic form in which two repeat units compose a tandem repeat will be referred to as 2R. These polymorphic form nucleotide sequences can be found in a DNA database (3R: GenBank accession number AF279906, 2R: GenBank accession number AF279907). An oligonucleotide of this invention has a nucleotide sequence that is complementary to the nucleotide sequence constituting a region comprising two units of these polymorphic forms, which are the central repeat unit of 3R, and the repeat unit located downstream of the central repeat unit. More specifically, 132-193 of the nucleotide sequence disclosed in GenBank Accession No. AF279906 is the region indicated in the above-mentioned (a). In the present invention, the complementary nucleotide sequences specifically include the following two nucleotide sequences:

(1) a nucleotide sequence determined to be complementary to a certain nucleotide sequence according to the Watson-Crick rule, or (2) a nucleotide sequence having a homology of 80% or more with the nucleotide sequence of (1).

Preferably, (2) includes a nucleotide sequence having a homology of 90% or more, more preferably, 95% or more, and even more preferably, 97% or more with the nucleotide sequence of (1). Algorithms for determining nucleotide sequence homology are well known. For example, programs for calculating nucleotide sequence homology using BLAST are in practical use. These programs can be used via the Internet.

The present inventors completed this invention by discovering that the two polymorphic forms can be distinguished when an oligonucleotide having such a nucleotide sequence is hybridized to genomic DNA under the same conditions. That is, the oligonucleotide hybridizes to a 3R tandem repeat, but does not hybridize to 2R under the same conditions.

Furthermore, the oligonucleotide of this invention hybridizes to the region under highly stringent hybridization conditions. In the present invention, "highly stringent hybridization conditions" can be achieved by simultaneously fulfilling the following conditions of (1) and (2). Incidentally, "does not substantially hybridize" means that no hybridization is detected under the same conditions as (1) described below:

(1) a certain oligonucleotide hybridizes to the region of (a), and (2) the oligonucleotide does not substantially hybridize to the tandem repeat consisting of two repeat units, which is another polymorphic form of the gene.

In the present invention, preferable oligonucleotide hybridizes to the 3' end repeat unit of the two repeat units composing a tandem repeat in the promoter region of the thymidylate synthase gene, under hybridization conditions that are less stringent than (b). The oligonucleotide is useful for the melting curve analysis of the present invention.

The oligonucleotide fulfilling the above-mentioned conditions is sometimes referred to as a mutation probe in this invention. The repeat units constituting the promoter of the thymidylate synthase gene are not completely identical. The nucleotide sequence of each of the three repeat units composing a tandem repeat in the promoter region of the thymidylate synthase gene is shown below.

5'-ccgcgccacttggcctgcctccgtcccg ccgcgccacttcgcctgcctc-cgtcccg ccgcgccacttcgcctgcctccgtcccccgcccg-3' (SEQ ID NO:5)

Therefore, an oligonucleotide that hybridizes to a specific repeat unit may not hybridize to other repeat units. The oligonucleotide of this invention was designed by utilizing such a phenomena. A preferable oligonucleotide of this invention is an oligonucleotide comprising the nucleotide sequence of SEQ ID NO: 1. A method for synthesizing an oligonucleotide having a nucleotide sequence of interest is known to those skilled in the art.

The oligonucleotides of this invention can be used to identify the number of tandem repeats in the promoter region of the thymidylate synthase gene. That is, the present invention relates to a method for identifying the number of tandem repeats in the promoter region of the thymidylate synthase gene comprising the steps of:

(a) amplifying a genomic DNA that comprises tandem repeats in at least the promoter region of the thymidylate synthase gene, (b) hybridizing the oligonucleotide of the present invention to the amplified genomic DNA of step (a) under stringent conditions, (c) detecting a hybridization between the oligonucleotide and the genomic DNA, and (d) identifying the number of tandem repeats as "two" when a hybridization is not detected, identifying the number of tandem repeats as "three" when a hybridization is detected.

Preferably, the method of present invention further comprising:

(e) hybridization the oligonucleotide of the present invention to the amplified genomic DNA of step (a) under hybridization conditions that are less stringent than (b), (f) detecting a hybridization between the oligonucleotide and the genomic DNA, and (g) identifying the number of tandem repeats as "two" when hybridization is not detected in (c) but is detected in (f)

In the present invention, genomic DNA can be obtained from a biological sample from a subject whose number of tandem repeats in the promoter region of the thymidylate synthase gene is to be identified. For example, a method for obtaining genomic DNA from blood cells collected from a subject is well known. Any method that can amplify DNA in a nucleotide sequence specific manner can be utilized to amplify genomic DNA. Generally, the PCR method is used to amplify genomic DNA. When amplifying DNA, it is sufficient to amplify an arbitrary region containing tandem repeats in at least the promoter region of the thymidylate synthase gene. More specifically, genomic DNA of at least 90 by that contains tandem repeats can be selected as the region to be amplified. For example, when detecting hybridization by melting curve analysis using LightCycler as described below, the length of the DNA to be amplified is usually 700 by or less.

The method of this invention for identifying the number of tandem repeats in the promoter region of the thymidylate synthase gene includes the step of hybridizing the mutation probe to the amplified genomic DNA under stringent conditions. Among the polymorphic forms in the promoter region of the thymidylate synthase gene, the mutation probe hybridizes to 3R, but not to 2R. Therefore, using hybridization of the mutation probe as an index, the number of tandem repeats can be determined. To detect the hybridization of the mutation probe, an arbitrary method for detecting DNA hybridization can be used.

In the present invention, melting curve analysis is the preferred method for detecting differences in nucleotide sequences using DNA hybridization. Certain oligonucleotides hybridize to polynucleotides having complementary sequences. Although DNA hybridization is sequence-specific, it is difficult to completely exclude hybridizations towards very similar nucleotide sequences. Melting curve analysis is a method for detecting changes in hybridization based on changes in melting temperature (Tm). Double strand DNA (dsDNA) formed by hybridization of nucleotide sequences that are complementary to each other, gradually dissociate and become single strand DNA (ss DNA) when the temperature is raised. When the relationship between the change from ds DNA to ss DNA and the change in temperature is plotted on a graph, the change into ss DNA is not linear, and occurs abruptly at a certain temperature. The temperature at which this abrupt change to ss DNA occurs is Tm. Tm changes with various factors such as nucleotide sequence, and composition of the solution in which the DNA exists. However, under specific conditions, Tm clearly changes depending on the nucleotide sequence, when there is a difference in a nucleotide sequence. Therefore, differences in Tm of a certain oligonucleotide towards a target sequence can be detected easily, even if the difference in the target sequence is slight. Melting curve analysis is a method that facilitates sensitive detection of slight differences in nucleotide sequences based on differences in Tm detected as above.

To carry out the method of this invention based on melting curve analysis, the difference in Tms of the mutation probe towards 3R and 2R can be detected. In melting curve analysis, the hybridization of a mutation probe towards a target sequence must be observed. There are no limitations on the method for observing hybridization. In the present invention, a preferred method for observing hybridization includes the application of fluorescence resonance energy transfer (FRET). FRET is a method for detecting hybridization utilizing the fact that two oligonucleotides that hybridize to adjacent regions on a target sequence come in close proximity to each other due to hybridization. The ends of the two adjacent oligonucleotides are labeled with different fluorophores that function as a donor or an acceptor. When the two come into close proximity due to hybridization, a characteristic fluorescence emission can be detected due to the energy transfer between the fluorophores.

To apply the FRET to the method of this invention, a second oligonucleotide that hybridizes to the region adjacent to the mutation probe is necessary for detecting the hybridization of the mutation probe. The present inventors discovered that when using as the mutation probe an oligonucleotide having the aforementioned properties (a) and (b), an oligonucleotide that can hybridize to the 5' side thereof is useful as the second oligonucleotide. More specifically, the present invention relates to an isolated oligonucleotide that hybridizes to the region adjacent to the 5' side of the oligonucleotide that:

(a) comprises a nucleotide sequence that is complementary to a region consisting of:
  (i) the central repeat unit of three repeat units composing a tandem repeat in the promoter region of the thymidylate synthase gene, and
  (ii) the repeat unit located downstream of the central repeat unit, and
(b) hybridizes to the region of (a).

In the present invention, "the region adjacent to the 5' side of the oligonucleotide" refers to the 5' side region of the region to which the oligonucleotide hybridizes on the target nucleotide. "Adjacent to" includes the case where the ends of the oligonucleotide and the second oligonucleotide are −0 to 10 bases apart, and preferably 0 to 5 bases. In the present invention, when using the second oligonucleotide for FRET, it is sometimes called an anchor probe. It is preferred that the Tm of the anchor probe is the same or more than the Tm of the mutation probe towards a 3R tandem repeat. The relationship between genomic DNA and each probe is indicated in FIG. 1.

Hybridization of the mutation probe can be observed by FRET while performing PCR. That is, hybridization of the mutation probe can be detected while amplifying genomic DNA. To detect hybridization of the mutation probe during PCR, it is preferable to design the Tm of the mutation probe and anchor probe in such a way that hybridization to the amplicon takes place during the annealing phase of PCR. To adjust the Tm to an appropriate range, mismatched bases can be included in the nucleotide sequences of the mutation probe and the anchor probe. Furthermore, it is preferred that the 3' end of each probe is modified to avoid extension of the probes by DNA polymerase. For example, an oligonucleotide labeled at its 5' end with a fluorophore can be modified at its 3' end by phosphorylation.

An instrument that uses FRET to detect hybridization of the mutation probe during PCR is commercially available. For example, LightCycler™ is equipped with the mechanism and software necessary for analyzing a PCR amplicon by FRET. The present invention can be carried out using such an instrument. A specific protocol for carrying out the method of this invention by LightCycler™ using the mutation probe and the anchor probe is described below.

Genomic DNA that comprises tandem repeats in at least the promoter region of the thymidylate synthase gene is amplified with specific primers from human genomic DNA. The amplicon is detected by fluorescence using the mutation probe and the anchor probe as a specific pair of Hybridization Probes. The Hybridization Probes consist of two different short oligonucleotides that hybridize to an internal sequence of the amplified fragment during the annealing phase of the PCR cycle. One probe (mutation probe) is labeled at the 5'-end with LightCycler-Red 640, and to avoid extension, modified at the 3'-end by phosphorylation. The second probe (anchor probe) is labeled at the 3'-end with fluorescein. Only after hybridization to the template DNA do the two probes come in close proximity, resulting in fluorescence resonance energy transfer (FRET) between the two fluorophores. During FRET, fluorescein, the donor fluorophore, is excited by the light source of the LightCycler Instrument, and part of the excitation energy is transferred to LightCycler-Red 640, the acceptor fluorophore. The emitted fluorescence of LightCycler-Red 640 is then measured by the LightCycler Instrument.

The oligonucleotides of the present invention are also used to determine the genotype by performing a melting curve analysis after the amplification cycles are completed and the amplicon is formed.

The fluorescein-labeled oligonucleotide of the present invention hybridizes to a part of the target sequence that is not mutated and functions as an anchor probe.

The other oligonucleotide, labeled with Light Cycler-Red640, spans the repeat unit (mutation probe). The latter probe has a lower melting temperature (Tm) than the anchor probe, thus ensuring that the fluorescent signal generated during the melting curve analysis is determined only by the mutation probe. The Tm is not only dependent on the length and G+C content, but also on the degree of homology between the mutation probe and the template DNA. When a 2R type tandem repeat is present, the mismatch of the mutation probe with the target destabilizes the hybrid. With a 3R type tandem repeat, mismatches do not occur, and the hybrid has a higher Tm. The temperature is slowly increased and when the mutation probe melts off and the two fluorescent dyes are no longer in close proximity, the fluorescence will decrease. For mutated genotypes, this will occur at temperatures lower than that for the wildtype genotype.

The 5R type tandem repeat of the thymidylate synthase has been reported recently (Luo H R, Lu X M, Yao Y G, Horie N, Takeishi K, Jorde L B, Zhang Y P. (2002) Length polymorphism of thymidylate synthase regulatory region in Chinese populations and evolution of the novel alleles. Biochem Genet 40(1-2): 41-51). The mutation probe of the present invention will hybridize to the 5R type tandem repeat besides the 3R type one. However, it does not make significant difference whether the probe can distinguish between the 3R type and 5R type. The genotyping and prediction for responsiveness in the present invention can be carried out whenever the probe can distinguish the 2R type that possesses high responsiveness from other polymorphic types.

As described above, the genotype of the thymidylate synthase gene is elucidated based on the number of tandem repeats determined by the present invention. More specifically the present invention provides a method for genotyping the thymidylate synthase gene of a subject, the method comprising:
(a) identifying the number of tandem repeats in the promoter region of the thymidylate synthase gene by the method of present invention, and
(b) determining that the thymidylate synthase genotype of the subject is "homozygous 2R/2R" when the number of tandem repeats is identified as only two, "homozygous 3R/3R" when the number of tandem repeats is identified as only three, or "heterozygous 2R/3R" when the number of tandem repeats is identified as both "two" and "three".

There is a report that used the LightCycler for genotyping of other genes (Nicolas Von Ahsen et al. Clinical Chemistry 46: 12, 1939-1945 (2000), DNA base bulge vs. unmatched end formation in probe-based diagnostic insertion/deletion genotyping: Genotyping the UGT1A1 (TA)n polymorphism by real-time fluorescence PCR). However, the LightCycler has not been used for genotyping the thymidylate synthase gene prior to the present invention.

Based on the thymidylate synthase genotype elucidated, the responsiveness of a subject towards an antitumor agent targeting thymidylate synthase can be predicted. More specifically, the present invention provides a method for predicting the responsiveness of a subject towards an antitumor agent targeting thymidylate synthase, the method comprising:
(a) determining the thymidylate synthase genotype of the subject by the method of the invention, and
(b) associating the thymidylate synthase genotype with the responsiveness of the subject towards an antitumor agent targeting thymidylate synthase.

In the present invention, "predicting the responsiveness of a subject towards an antitumor agent targeting thymidylate synthase" refers to the prediction of the degree of cytotoxic activity of an antitumor agent targeting thymidylate synthase towards a certain patient and/or a tumor tissue obtained from a patient. As mentioned earlier, thymidylate synthase genotype is a major factor determining the expression level of thymidylate synthase. Furthermore, the expression level of thymidylate synthase is related to the responsiveness of a subject towards an antitumor agent targeting thymidylate synthase. That is, the expression level of thymidylate synthase is inversely correlated to the responsiveness. Therefore, the genotype and the responsiveness can be correlated. Specifically, based on the present invention, a subject whose thymidylate synthase genotype has been determined to be homozygous 2R/2R is predicted to have high responsiveness. That is, in this subject, the cytotoxic activity of the antitumor agent targeting thymidylate synthase is predicted to be high. On the other hand, a subject whose genotype has been determined to be 2R/3R heterozygous, or 3R/3R homozygous is predicted to have a normal responsiveness. That is, in this subject, it is predicted that the antitumor agent targeting thymidylate synthase will have a normal cytotoxic activity "Normal cytotoxic activity" refers to a condition in which the possibility of having severe adverse drug effects is not high when the drug is administered according to a usual administration protocol. Alternately, it refers to a condition in which the inhibitory action of a drug on tumor tissues cannot be expected unless the dose is based on a normal administration protocol.

In the present invention, the antitumor agent targeting thymidylate synthase includes an antitumor agent having an action to adjust the activity of thymidylate synthase directly or indirectly. One of the modes of action of a 5-FU-type antitumor agent is inhibiting the activity of thymidylate synthase by its metabolite, FdUMP. Thymidylate synthase is the direct target enzyme of 5-FU-type antitumor agents. On the other hand, responsiveness towards Methotrexate used for treating leukemia and such, is also thought to be related to the thymidylate synthase genotype (The Lancet Vol. 359, 1033-1034, Mar. 23, 2002). Methotrexate is an inhibitor of dihydrofolate reductase. On the other hand, the reaction catalyzed by thymidylate synthase requires reduction of dihydrofolate. That is, Methotrexate is an antitumor agent that indirectly inhibits thymidylate synthase. The method of this invention allows the prediction of the responsiveness towards such antitumor agents that have indirect inhibitory actions on thymidylate synthase. Examples of antitumor agents for which the responsiveness can be predicted by the method of this invention are 5-FU, Carmofur, Tegafur, UFT, S-1, Doxifluridine, Capecitabine, Fludarabine, Methotrexate, Leucovorin, and Levofolinate.

Based on responsiveness determined in this manner, a chemotherapy method for cancer can be designed. More specifically, the present invention relates to a method for determining the dose and/or the type of an antitumor agent that targets thymidylate synthase for treating a cancer patient, the method comprising:
(a) determining the thymidylate synthase genotype of the patient by the method of the present invention, and
(b) for a "homozygous 2R/2R" patient, deciding to: (i) administer an antitumor agent dose that is lower than the normally used dose, or (ii) use an antitumor agent that has a different target.

For patients predicted to have a high responsiveness towards an antitumor agent that targets thymidylate synthase, lowering the dose of the antitumor agent, or selecting an antitumor agent having a different target is recommended. As a result, the danger of exposing a patient to adverse drug effects can be decreased.

Additionally, the present invention provides a kit for identifying the number of tandem repeats in the promoter region of the thymidylate synthase gene, the kit comprising:
(a) an oligonucleotide comprising the nucleotide sequence of SEQ ID NO: 1, and
(b) an oligonucleotide comprising the nucleotide sequence of SEQ ID NO: 2.

As mentioned earlier, the oligonucleotides constituting the kit of this invention can be labeled with a fluorophore for FRET. Furthermore, additional factors can be combined with the kit of this invention. Examples of additional factors are:
- hybridization buffer,
- control sample that yields the result of 2R and/or 3R, and
- DNA polymerase and substances for PCR.

Any patents, patent applications, and publications cited herein are incorporated by reference.

BRIEF DESCRIPTION OF THE DRAWINGS

FIG. 1 shows the relationship between tandem repeats of 2R (SEQ ID NO:6) and 3R (SEQ ID NO:7), and two probes that hybridize to the tandem repeats. The nucleotide sequences in the figure indicate the anchor probe (top; SEQ ID NO:2), the tandem repeats of genomic DNA (middle), and the mutation probe (bottom; SEQ ID NO:1). The sequences of the repeat units are in italics. Each repeat unit is separated by a space. All sequences are shown as the sequence of the sense strand for easy verification of the sequences. In reality, either one of the genomic DNA and each probe is an antisense sequence.

EXAMPLES

1) Extraction of DNA

Genomic DNA was purified from 100 nl of human whole blood. For the purification, GFX™ Genomic Blood DNA Purification Kit (Amersham Pharmacia Biotech) was used.

2) Sequences of PCR Primer FW, PCR Primer REV, Hybridization Probe (Anchor), and Hybridization Probe (Mutation)

```
PCR Forward Primer Sequence
                                              (SEQ ID NO: 3)
5'-GTG GCT CCT GCG TTT CCC C-3'

PCR Reverse Primer Sequence
                                              (SEQ ID NO: 4)
5'-TCC GAG CCG GCC ACA GGC AT-3'

Hybridization probe (Anchor) Sequence
                                              (SEQ ID NO: 2)
5'-CGC GGA AGG GGT CCT GCC ACC GCG CCA CTT GGC
CTG CCT CGG TCC CGC CG-FITC-3'

Hybridization probe (Mutation) Sequence
                                              (SEQ ID NO: 1)
5'-LCRed640-CTT GGC CTG CCT CCG TCC CGC CGC GCC-
phosphorylation-3'
```

Primers were synthesized by SAWADY Technology Co., Ltd., and probes were synthesized by Nihon Gene Research Lab's, Inc.

3) Preparation of PCR Mixture

LightCycler-FastStart DNA Master SYBR Green I Kit (Roche Diagnostics) was used. The PCR mixture was prepared from the following compositions.

| | |
|---|---|
| PCR Grade Distilled Water (attached to Kit) | 5.4 μl |
| 10 μM Forward Primer | 1 μl (final conc. 0.5 μM) |
| 10 μM Reverse Primer | 1 μl (final conc. 0.5 μM) |
| 4 pmol/μl Hybridization probe (Anchor) | 1 μl |
| 4 pmol/μl Hybridization probe (Mutation) | 1 μl |
| 25 mM MgCl$_2$ (attached to Kit) | 2.4 μl (final conc. 4 mM) |
| DMSO | 1.2 μl |
| Hybridization master mix (attached to Kit) | 2 μl |
| Human Blood Genomic DNA solution | 5 μl |
| Total volume | 20 μl |

4) PCR Using LightCycler

Experimental Protocol for PCR using the LightCycler Experimental Protocol

| | | | Type | None | | Cycles | 1 |
|---|---|---|---|---|---|---|---|
| Program Segment Number | Denature Temperature Target (° C.) | Hold Time (sec) | Slope (° C./sec) | 2° Target Temp (° C.) | Step Size (° C.) | Step Delay (Cycles) | Acquisition Mode |
| 1 | 95 | 300 | 20 | 0 | 0 | 0 | None |

| | | | Type | Quantification | | Cycles | 33 |
|---|---|---|---|---|---|---|---|
| Program Segment Number | PCR Temperature Target (° C.) | Hold Time (sec) | Slope (° C./sec) | 2° Target Temp (° C.) | Step Size (° C.) | Step Delay (Cycles) | Acquisition Mode |
| 1 | 95 | 15 | 20 | 0 | 0 | 0 | None |
| 2 | 58 | 5 | 20 | 0 | 0 | 0 | Single |
| 3 | 72 | 12 | 20 | 0 | 0 | 0 | None |

| | | | Type | Melting Curve | | Cycles | 1 |
|---|---|---|---|---|---|---|---|
| Program Segment Number | Melting Temperature Target (° C.) | Hold Time (sec) | Slope (° C./sec) | 2° Target Temp (° C.) | Step Size (° C.) | Step Delay (Cycles) | Acquisition Mode |
| 1 | 95 | 3 | 20 | 0 | 0 | 0 | None |
| 2 | 77 | 30 | 0.5 | 0 | 0 | 0 | None |
| 3 | 70 | 30 | 0.2 | 0 | 0 | 0 | None |

-continued

| | | | | | | | |
|---|---|---|---|---|---|---|---|
| 4 | 56 | 30 | 0.2 | 0 | 0 | 0 | None |
| 5 | 95 | 0 | 0.1 | 0 | 0 | 0 | Continuous |

| | | | Type | None | | Cycles | 1 |
|---|---|---|---|---|---|---|---|
| Program Segment Number | Cooling Temperature Target (° C.) | Hold Time (sec) | Slope (° C./sec) | 2° Target Temp (° C.) | Step Size (° C.) | Step Delay (Cycles) | Acquisition Mode |
| 1 | 40 | 30 | 20 | 0 | 0 | 0 | None |

5) Melting Curve Analysis Using LightCycler

Analysis was performed by using the melting curves program of LightCycler. Fluorescence was set to F2/F1. The "Calculation method" of "Step 1: Melting Peaks" was set to "Linear with Background Correction". To adjust the base line, the cursor at the low temperature side (Green) was set to around 62° C. and cursor at the high temperature side was set to around 83° C. To calculate the melting peak area, "Step 2: Peak Areas" was selected, and the number of peaks were chosen for each sample to obtain the Tm Value, peak area, and standard deviation.

6) Determination

A sequence whose peak Tm value was only 68-70° C. was determined to be 2R/2R homozygous, and a sequence whose peak Tm value was only 76-79° C. was determined to be 3R/3R homozygous. A sequence which had both Tm values was determined to be 2R/3R heterozygous.

Oligonucleotides for genotyping the thymidylate synthase gene are provided. The number of tandem repeats in the promoter region of the thymidylate synthase gene can be identified based on the hybridization of an oligonucleotide to the genomic DNA. The identification based on hybridization is simple and fast compared to gel electrophoresis. Using the oligonucleotides of this invention, the number of tandem repeats can be identified easily using mismatches as indexes.

Therefore, the genotype of the thymidylate synthase gene can be determined based on the number of tandem repeats. The genotype relates to the responsiveness of a subject towards an antitumor agent targeting thymidylate synthase. Therefore, based on the present invention, it is possible to predict the responsiveness towards an antitumor agent targeting thymidylate synthase. Furthermore, based on the responsiveness predicted according to the present invention, a chemotherapy method for cancer can be designed. More specifically, for patients predicted to have a high responsiveness towards an antitumor agent targeting thymidylate synthase, lowering the dose of the antitumor agent, or selecting an antitumor agent having a different target is recommended. As a result, the danger of exposing a patient to adverse drug effects can be reduced.

The invention claimed is:

1. A method for identifying a number of tandem repeats in the promoter region of a thymidylate synthase gene, the method comprising:
   (a) amplifying a genomic DNA that comprises tandem repeats in at least the promoter region of the thymidylate synthase gene;
   (b) contacting, under stringent hybridization conditions, the amplified genomic DNA with either (i) a first oligonucleotide comprising the nucleotide sequence of SEQ ID NO:1 and a second oligonucleotide comprising the nucleotide sequence of SEQ ID NO:2, or (ii) a first oligonucleotide comprising the nucleotide sequence of the exact complement of SEQ ID NO:1 and a second oligonucleotide comprising the nucleotide sequence of the exact complement of SEQ ID NO:2, wherein the hybridization conditions are such that hybridization between the first oligonucleotide and the amplified genomic DNA can be detected if three tandem repeats are present, but not if only two tandem repeats are present;
   (c) detecting whether hybridization between the first oligonucleotide and the amplified genomic DNA has occurred; and
   (d) identifying the number of tandem repeats as "two" when hybridization is not detected.

2. The method of claim 1, wherein step (c) comprises melting curve analysis.

3. The method of claim 1, wherein the nucleotide sequence of the first oligonucleotide comprises SEQ ID NO:1.

4. The method of claim 1, the method comprising detecting fluorescence resonance energy transfer using
   a first fluorescent dye at the 5' end of the first oligonucleotide and a second fluorescent dye at the 3' end of the second oligonucleotide, wherein the first fluorescent dye transfers fluorescence resonance energy to the second fluorescent dye or vice versa.

5. The method of claim 1, wherein the nucleotide sequence of the first oligonucleotide consists of SEQ ID NO:1.

6. The method of claim 4, wherein the nucleotide sequence of the first oligonucleotide comprises SEQ ID NO:1.

7. The method of claim 4, wherein the nucleotide sequence of the first oligonucleotide consists of SEQ ID NO:1.

8. The method of claim 4, wherein the nucleotide sequence of the second oligonucleotide comprises SEQ ID NO:2.

9. The method of claim 4, wherein the nucleotide sequence of the second oligonucleotide consists of SEQ ID NO:2.

10. The method of claim 4, wherein the first and second fluorescent dyes are selected from FITC, RED640, and RED705.

11. A method for genotyping a thymidylate synthase gene of a subject, the method comprising:
  (a) identifying the number of tandem repeats in the promoter region of the thymidylate synthase gene by the method of claim 1, and
  (b) determining that the thymidylate synthase genotype of the subject is "homozygous 2R/2R" when the number of tandem repeats is identified as two.

12. A method for predicting the responsiveness of a subject toward an antitumor agent targeting thymidylate synthase, the method comprising:
  (a) determining the thymidylate synthase genotype of the subject by the method of claim 11, and
  (b) associating the thymidylate synthase genotype with the responsiveness of the subject towards an antitumor agent targeting thymidylate synthase.

13. A method for determining the dose and/or the type of an antitumor agent targeting thymidylate synthase for treating a cancer patient, the method comprising:
  (a) determining the thymidylate synthase genotype of the patient by the method of claim 11, and
  (b) for a "homozygous 2R/2R" patient, deciding to: (i) administer an antitumor agent dose that is lower than the normally used dose, or (ii) use an antitumor agent that has a different target.

14. The method of claim 1, wherein the nucleotide sequence of the second oligonucleotide comprises SEQ ID NO:2.

15. The method of claim 1, wherein the nucleotide sequence of the second oligonucleotide consists of SEQ ID NO:2.

16. The method of claim 1, wherein the 3' end of the first oligonucleotide is phosphorylated.

17. A method for identifying a number of tandem repeats in the promoter region of a thymidylate synthase gene, the method comprising:
  (a) amplifying a genomic DNA that comprises tandem repeats in at least the promoter region of the thymidylate synthase gene;
  (b) contacting, under stringent hybridization conditions, the amplified genomic DNA with either (i) a first oligonucleotide comprising the nucleotide sequence of SEQ ID NO:1 and a second oligonucleotide comprising the nucleotide sequence of SEQ ID NO:2, or (ii) a first oligonucleotide comprising the nucleotide sequence of the exact complement of SEQ ID NO:1 and a second oligonucleotide comprising the nucleotide sequence of the exact complement of SEQ ID NO:2, wherein the hybridization conditions are such that hybridization between the first oligonucleotide and the amplified genomic DNA can be detected if three tandem repeats are present, but not if only two tandem repeats are present;
  (c) detecting whether hybridization between the first oligonucleotide and the amplified genomic DNA has occurred;
  (d) contacting the first and second oligonucleotides with the amplified genomic DNA of step (a) under hybridization conditions that are less stringent than in step (b);
  (e) detecting whether hybridization between the first oligonucleotide and the amplified genomic DNA has occurred in (d); and
  (f) identifying the number of tandem repeats as "two" when hybridization is not detected in (c), but is detected in (e).

18. The method of claim 17, wherein steps (c) and (e) comprise melting curve analysis.

19. The method of claim 17, the method comprising detecting fluorescence resonance energy transfer using a first fluorescent dye at the 5' end of the first oligonucleotide and a second fluorescent dye at the 3' end of the second oligonucleotide, wherein the first fluorescent dye transfers fluorescence resonance energy to the second fluorescent dye or vice versa.

20. The method of claim 17, wherein the nucleotide sequence of the first oligonucleotide comprises SEQ ID NO:1.

21. The method of claim 17, wherein the nucleotide sequence of the first oligonucleotide consists of SEQ ID NO:1.

22. The method of claim 17, wherein the nucleotide sequence of the second oligonucleotide comprises SEQ ID NO:2.

23. The method of claim 17, wherein the nucleotide sequence of the second oligonucleotide consists of SEQ ID NO:2.

24. The method of claim 19, wherein the nucleotide sequence of the first oligonucleotide comprises SEQ ID NO:1.

25. The method of claim 19, wherein the nucleotide sequence of the first oligonucleotide consists of SEQ ID NO:1.

26. The method of claim 19, wherein the nucleotide sequence of the second oligonucleotide comprises SEQ ID NO:2.

27. The method of claim 19, wherein the nucleotide sequence of the second oligonucleotide consists of SEQ ID NO:2.

28. The method of claim 19, wherein the first and second fluorescent dyes are selected from FITC, RED640, and RED705.

29. The method of claim 17, wherein the 3' end of the first oligonucleotide is phosphorylated.

30. A method for genotyping a thymidylate synthase gene of a subject, the method comprising:
  (a) identifying the number of tandem repeats in the promoter region of the thymidylate synthase gene by the method of claim 17, and
  (b) determining that the thymidylate synthase genotype of the subject is "homozygous 2R/2R" when the number of tandem repeats is identified as two.

31. A method for identifying a number of tandem repeats in the promoter region of a thymidylate synthase gene, the method comprising:
  (a) amplifying a genomic DNA that comprises tandem repeats in at least the promoter region of the thymidylate synthase gene;
  (b) hybridizing a sample of the amplified genomic DNA with either (i) a first oligonucleotide comprising the nucleotide sequence of SEQ ID NO:1 and a second oligonucleotide comprising the nucleotide sequence of SEQ ID NO:2, or (ii) a first oligonucleotide comprising the nucleotide sequence of the exact complement of SEQ ID NO:1 and a second oligonucleotide comprising the nucleotide sequence of the exact complement of SEQ ID NO:2;

(c) subjecting the sample to melting curve analysis to determine the melting temperature (Tm);

(d) comparing the Tm determined in (c) to the Tm obtained with the first oligonucleotide in each of two controls: a two tandem repeat (2R) control and a three tandem repeat (3R) control; and (e) identifying the number of tandem repeats as "two" when the Tm determined in (c) is more similar to the Tm obtained in the two tandem repeat control than to the Tm obtained in the three tandem repeat control.

32. The method of claim 31, the method comprising detecting fluorescence resonance energy transfer using a first fluorescent dye at the 5' end of the first oligonucleotide and a second fluorescent dye at the 3' end of the second oligonucleotide, wherein the first fluorescent dye transfers fluorescence resonance energy to the second fluorescent dye or vice versa.

33. The method of claim 31, wherein the nucleotide sequence of the first oligonucleotide comprises SEQ ID NO:1.

34. The method of claim 31, wherein the nucleotide sequence of the first oligonucleotide consists of SEQ ID NO:1.

35. The method of claim 31, wherein the nucleotide sequence of the second oligonucleotide comprises SEQ ID NO:2.

36. The method of claim 31, wherein the nucleotide sequence of the second oligonucleotide consists of SEQ ID NO:2.

37. The method of claim 32, wherein the nucleotide sequence of the first oligonucleotide comprises SEQ ID NO:1.

38. The method of claim 32, wherein the nucleotide sequence of the first oligonucleotide consists of SEQ ID NO:1.

39. The method of claim 32, wherein the nucleotide sequence of the second oligonucleotide comprises SEQ ID NO:2.

40. The method of claim 32, wherein the nucleotide sequence of the second oligonucleotide consists of SEQ ID NO:2.

41. The method of claim 32, wherein the first and second fluorescent dyes are selected from FITC, RED640, and RED705.

42. The method of claim 31, wherein the 3' end of the first oligonucleotide is phosphorylated.

43. A method for genotyping a thymidylate synthase gene of a subject, the method comprising:
(a) identifying the number of tandem repeats in the promoter region of the thymidylate synthase gene by the method of claim 31, and
(b) determining that the thymidylate synthase genotype of the subject is "homozygous 2R/2R" when the number of tandem repeats is identified as two.

44. A method for identifying a number of tandem repeats in the promoter region of a thymidylate synthase gene, the method comprising:
(a) amplifying a genomic DNA that comprises tandem repeats in at least the promoter region of the thymidylate synthase gene;

(b) hybridizing a sample of the amplified genomic DNA with either (i) a first oligonucleotide comprising the nucleotide sequence of SEQ ID NO:1 and a second oligonucleotide comprising the nucleotide sequence of SEQ ID NO:2, or (ii) a first oligonucleotide comprising the nucleotide sequence of the exact complement of SEQ ID NO:1 and a second oligonucleotide comprising the nucleotide sequence of the exact complement of SEQ ID NO:2;

(c) subjecting the sample to melting curve analysis to determine whether the sample's melting temperature (Tm) corresponds to a two tandem repeat Tm, a three tandem repeat Tm, or a combination thereof.

45. The method of claim 44, the method comprising detecting fluorescence resonance energy transfer using a first fluorescent dye at the 5' end of the first oligonucleotide and a second fluorescent dye at the 3' end of the second oligonucleotide, wherein the first fluorescent dye transfers fluorescence resonance energy to the second fluorescent dye or vice versa.

46. The method of claim 44, wherein the nucleotide sequence of the first oligonucleotide comprises SEQ ID NO:1.

47. The method of claim 44, wherein the nucleotide sequence of the first oligonucleotide consists of SEQ ID NO:1.

48. The method of claim 44, wherein the nucleotide sequence of the second oligonucleotide comprises SEQ ID NO:2.

49. The method of claim 44, wherein the nucleotide sequence of the second oligonucleotide consists of SEQ ID NO:2.

50. The method of claim 45, wherein the nucleotide sequence of the first oligonucleotide comprises SEQ ID NO:1.

51. The method of claim 45, wherein the nucleotide sequence of the first oligonucleotide consists of SEQ ID NO:1.

52. The method of claim 45, wherein the nucleotide sequence of the second oligonucleotide comprises SEQ ID NO:2.

53. The method of claim 45, wherein the nucleotide sequence of the second oligonucleotide consists of SEQ ID NO:2.

54. The method of claim 45, wherein the first and second fluorescent dyes are selected from FITC, RED640, and RED705.

55. The method of claim 44, wherein wherein the 3' end of the first oligonucleotide is phosphorylated.

56. A method for genotyping a thymidylate synthase gene of a subject, the method comprising:
(a) identifying the number of tandem repeats in the promoter region of the thymidylate synthase gene by the method of claim 44, and
(b) determining that the thymidylate synthase genotype of the subject is "homozygous 2R/2R" when the number of tandem repeats is identified as two.

57. A method for predicting the responsiveness of a subject toward an antitumor agent targeting thymidylate synthase, the method comprising:
(a) determining the thymidylate synthase genotype of the subject by the method of claim 30, and
(b) associating the thymidylate synthase genotype with the responsiveness of the subject towards an antitumor agent targeting thymidylate synthase.

58. A method for determining the dose and/or the type of an antitumor agent targeting thymidylate synthase for treating a cancer patient, the method comprising:

(a) determining the thymidylate synthase genotype of the patient by the method of claim 30, and (b) for a "homozygous 2R/2R" patient, deciding to: (i) administer an antitumor agent dose that is lower than the normally used dose, or (ii) use an antitumor agent that has a different target.

59. A method for predicting the responsiveness of a subject toward an antitumor agent targeting thymidylate synthase, the method comprising:

(a) determining the thymidylate synthase genotype of the subject by the method of claim 43, and (b) associating the thymidylate synthase genotype with the responsiveness of the subject towards an antitumor agent targeting thymidylate synthase.

60. A method for determining the dose and/or the type of an antitumor agent targeting thymidylate synthase for treating a cancer patient, the method comprising:

(a) determining the thymidylate synthase genotype of the patient by the method of claim 43, and (b) for a "homozygous 2R/2R" patient, deciding to: (i) administer an antitumor agent dose that is lower than the normally used dose, or (ii) use an antitumor agent that has a different target.

61. A method for predicting the responsiveness of a subject toward an antitumor agent targeting thymidylate synthase, the method comprising:

(a) determining the thymidylate synthase genotype of the subject by the method of claim 56, and (b) associating the thymidylate synthase genotype with the responsiveness of the subject towards an antitumor agent targeting thymidylate synthase.

62. A method for determining the dose and/or the type of an antitumor agent targeting thymidylate synthase for treating a cancer patient, the method comprising:

(a) determining the thymidylate synthase genotype of the patient by the method of claim 56, and (b) for a "homozygous 2R/2R" patient, deciding to: (i) administer an antitumor agent dose that is lower than the normally used dose, or (ii) use an antitumor agent that has a different target.

* * * * *

UNITED STATES PATENT AND TRADEMARK OFFICE
CERTIFICATE OF CORRECTION

PATENT NO. : 8,507,225 B2
APPLICATION NO. : 13/027751
DATED : August 13, 2013
INVENTOR(S) : Hideyuki Yasuno and Kazushige Mori It is certified that error appears in the above-identified patent and that said Letters Patent is hereby corrected as shown below:

On the Title Page, Item 56, Right Column (Other Publications), Etienne et al. publication: replace "Onocology" with -- Oncology --.

Title Page 2, Item 56, Left Column (Other Publications), Kawakami et al. publication: replace "Thrnslational" with -- Translational --.

Title Page 2, Item 56, Left Column (Other Publications), Kawakami et al. publication: replace "Reasearch" with -- Research --.

Title Page 2, Item 56, Right Column (Other Publications), Kawakami et al. publication: replace "Reasearch" with -- Research --.

In the Specification:

Column 4, Line 40: After "in (f)" insert -- . --.

Column 4, Line 52: Replace "90 by" with -- 90 bp --.

Column 4, Line 56: Replace "700 by" with -- 700 bp --.

Column 9, Line 26: Replace "100 nl" with -- 100 μl --.

In the Claims:

Column 18, Line 47: In Claim 55, replace "wherein wherein" with -- wherein --.

Signed and Sealed this
Fifth Day of November, 2013

Teresa Stanek Rea
*Deputy Director of the United States Patent and Trademark Office*

SEQUENCE LISTING

```
<160> NUMBER OF SEQ ID NOS: 7

<210> SEQ ID NO 1
<211> LENGTH: 27
<212> TYPE: DNA
<213> ORGANISM: Artificial Sequence
<220> FEATURE:
<223> OTHER INFORMATION: an artificially synthesized probe sequence
<220> FEATURE:
<221> NAME/KEY: misc_feature
<222> LOCATION: 1
<223> OTHER INFORMATION: labeled with Red640

<400> SEQUENCE: 1
cttggcctgc ctccgtcccg ccgcgcc                                        27

<210> SEQ ID NO 2
<211> LENGTH: 50
<212> TYPE: DNA
<213> ORGANISM: Artificial Sequence
<220> FEATURE:
<223> OTHER INFORMATION: an artificially synthesized probe sequence
<220> FEATURE:
<221> NAME/KEY: misc_feature
<222> LOCATION: 50
<223> OTHER INFORMATION: labeled with FITC

<400> SEQUENCE: 2
cgcggaaggg gtcctgccac cgcgccactt ggcctgcctc ggtcccgccg              50

<210> SEQ ID NO 3
<211> LENGTH: 19
```

```
<212> TYPE: DNA
<213> ORGANISM: Artificial Sequence
<220> FEATURE:
<223> OTHER INFORMATION: an artificially synthesized primer sequence

<400> SEQUENCE: 3
gtggctcctg cgtttcccc                                                   19

<210> SEQ ID NO 4
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 4
tccgagccgg ccacaggcat                                                  20

<210> SEQ ID NO 5
<211> LENGTH: 90
<212> TYPE: DNA
<213> ORGANISM: Homo sapiens

<400> SEQUENCE: 5
ccgcgccact tggcctgcct ccgtcccgcc gcgccacttc gcctgcctcc gtcccgccgc       60
gccacttcgc ctgcctccgt ccccgcccg                                        90

<210> SEQ ID NO 6
<211> LENGTH: 92
<212> TYPE: DNA
<213> ORGANISM: Homo sapiens

<400> SEQUENCE: 6
ggcgcgcgga aggggtcctg ccaccgcgcc acttggcctg cctccgtccc gccgcgccac       60
ttcgcctgcc tccgtccccc gcccgccgcg cc                                    92

<210> SEQ ID NO 7
<211> LENGTH: 113
<212> TYPE: DNA
<213> ORGANISM: Homo sapiens

<400> SEQUENCE: 7
ggcgcgcgga aggggtcctg ccaccgcgcc acttggcctg cctccgtccc gccgcgccac       60
ttcgcctgcc tccgtcccgc cgcgccactt cgcctgcctc cgtccccgc ccg             113
```